(12) United States Patent
Vincent

(10) Patent No.: US 10,681,932 B2
(45) Date of Patent: Jun. 16, 2020

(54) SPECIFIC BACTERIA FOR THEIR USE AS A MEDICAMENT, IN PARTICULAR FOR CONTROLLING EXCESS WEIGHT, OBESITY, CARDIOMETABOLIC DISEASES AND INFLAMMATORY BOWEL DISEASES

(71) Applicant: INTERNATIONAL NUTRITION RESEARCH COMPANY, Luxembourg (LU)

(72) Inventor: Claude Vincent, Bordeaux (FR)

(73) Assignee: INTERNATIONAL NUTRITION RESEARCH COMPANY, Luxembourg (LU)

( * ) Notice: Subject to any disclaimer, the term of this patent is extended or adjusted under 35 U.S.C. 154(b) by 0 days.

(21) Appl. No.: 15/591,389

(22) Filed: May 10, 2017

(65) Prior Publication Data
US 2018/0255819 A1    Sep. 13, 2018

(30) Foreign Application Priority Data

Mar. 10, 2017 (FR) .................................... 17 70237

(51) Int. Cl.
| | | |
|---|---|---|
| *A23L 33/135* | (2016.01) | |
| *A61K 9/00* | (2006.01) | |
| *A61P 3/00* | (2006.01) | |
| *C12N 1/20* | (2006.01) | |
| *A61P 3/04* | (2006.01) | |
| *A61K 35/74* | (2015.01) | |
| *A61K 35/00* | (2006.01) | |
| *C12R 1/145* | (2006.01) | |
| *C12R 1/01* | (2006.01) | |
| *A23P 10/30* | (2016.01) | |
| *A61K 45/06* | (2006.01) | |

(52) U.S. Cl.
CPC ............. *A23L 33/135* (2016.08); *A23P 10/30* (2016.08); *A61K 9/00* (2013.01); *A61K 9/0053* (2013.01); *A61K 35/74* (2013.01); *A61P 3/00* (2018.01); *A61P 3/04* (2018.01); *C12N 1/20* (2013.01); *C12R 1/01* (2013.01); *C12R 1/145* (2013.01); *A61K 35/00* (2013.01); *A61K 45/06* (2013.01); *A61K 2035/11* (2013.01)

(58) Field of Classification Search
CPC ............. A61K 2300/00; A61K 31/198; A61K 31/355; A61K 31/405; A61K 31/4415; A61K 31/519; A61K 31/59; A61K 33/06; A61K 33/24; A61K 33/30; A61K 31/202; A61K 35/741; A61K 2035/115; A61K 35/20; A61K 35/74; A61K 9/0056; A61K 9/19; A61K 31/185; A61K 31/201; A61K 38/17; A61K 31/00; A61K 31/575; A23V 2002/00; A23V 2200/332; A23V 2200/3204; A23V 2200/32; A23V 2200/328; A23V 2250/54246; A23V 2250/54252; C12Q 1/689; C12Q 2600/112; C12Q 2600/106; C12Q 2600/16; C12Q 1/6883; G06F 19/28; G06F 19/12; G06F 19/22; G06F 19/24; G06F 19/3418; G06F 19/3456; G06F 19/14; G06F 19/18; G06F 19/3437; G16H 50/20; G16H 50/50; Y02A 90/26; A23L 33/135; A23L 33/18; A23L 33/30; A23L 33/19

See application file for complete search history.

(56) References Cited

FOREIGN PATENT DOCUMENTS

WO    WO 2015/164555 A1 * 10/2015

OTHER PUBLICATIONS

WIPO document made available under the Patent Cooperation Treaty (PCT) of the Certified the priority document U.S. Appl. No. 61/983,094, received at the International Bureau May 3, 2015, 25 pages.*

* cited by examiner

*Primary Examiner* — Sarvamangala Devi
(74) *Attorney, Agent, or Firm* — Robin L. Teskin; Baker, Donelson, Bearman, Caldwell & Berkowitz PC

(57) ABSTRACT

The object of the invention are compositions and medical treatment methods with an inheritable, Gram-negative, strictly anaerobic and commensal bacterium of the family *Christensenellaceae* belonging to an OTU (Operational Taxonomic Unit) characterized by a 16S rRNA sequence SEQ ID NO: 1 or to an OTU characterized by a 16S rRNA sequence SEQ ID NO: 2.

11 Claims, 1 Drawing Sheet
Specification includes a Sequence Listing.

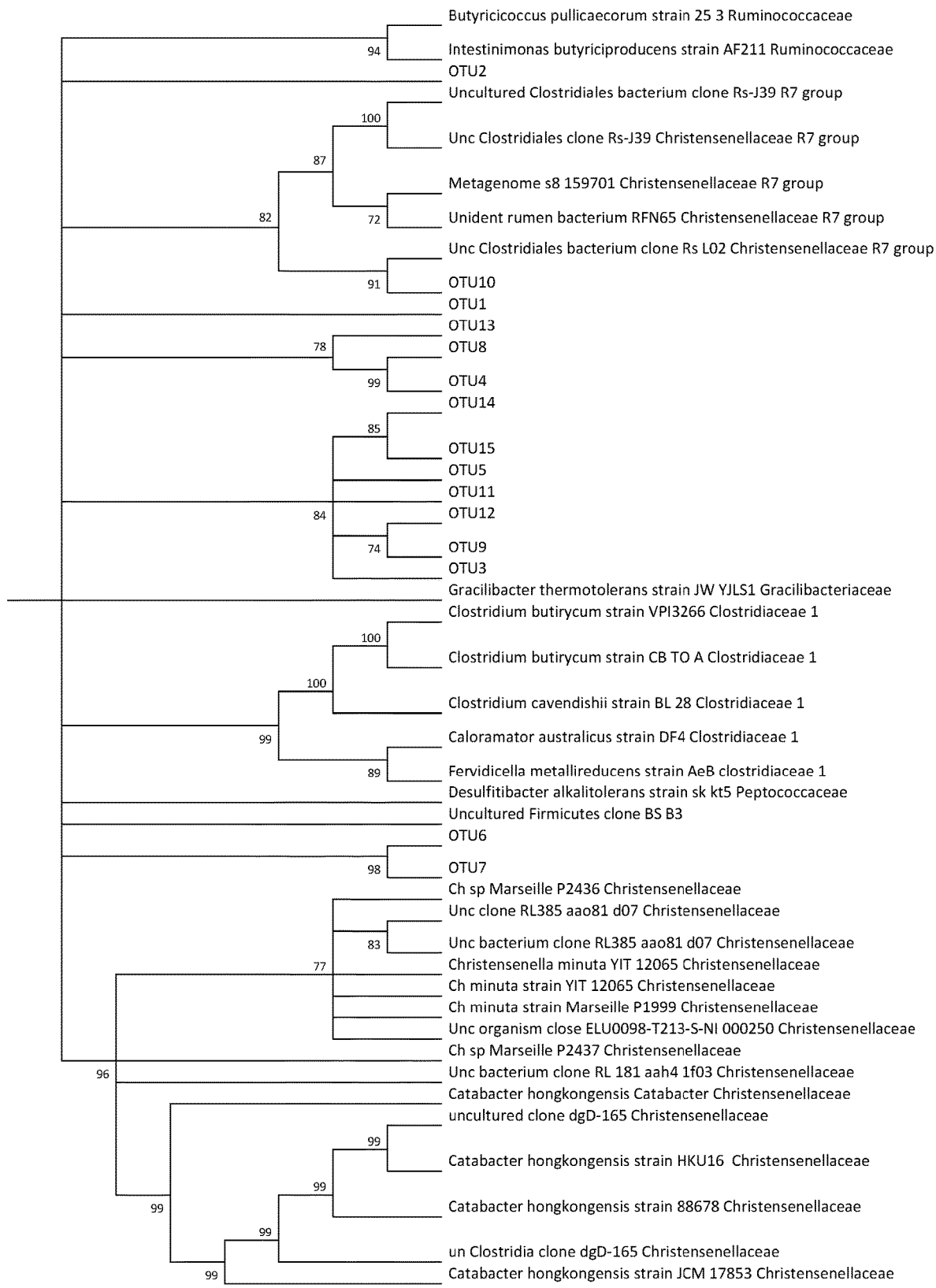

SPECIFIC BACTERIA FOR THEIR USE AS A MEDICAMENT, IN PARTICULAR FOR CONTROLLING EXCESS WEIGHT, OBESITY, CARDIOMETABOLIC DISEASES AND INFLAMMATORY BOWEL DISEASES

CROSS-REFERENCE TO RELATED APPLICATIONS

This application claims a benefit of priority to French patent application FR 1770237, filed on Mar. 10, 2017, the entire disclosure of which is incorporated herein by reference.

FIELD OF THE INVENTION

The present invention relates to particular bacteria for use as a medicament, in particular for preventing or controlling excess weight, obesity, cardiometabolic diseases and inflammatory bowel diseases. The invention also relates to compositions including such bacteria.

BACKGROUND SECTION

Excess weight and obesity now affect all populations, both in developed and developing countries. They are the cause of chronic diseases, such as, for the most part, cardiometabolic diseases, particularly diabetes and cardiovascular diseases, as well as certain cancers, neurodegenerative diseases and inflammatory bowel diseases, affecting a large part of the world's population and becoming the leading cause of death.

Modern medicament is helpless in the face of these chronic pathologies, whose management is more difficult, more time-consuming and less dichotomous than acute diseases. In addition, the durability of these diseases over time, with the aging of the population, has a considerable impact on public health spending, which is becoming unbearable.

Therefore, a first objective of the invention is to propose a simple, effective and economical solution for dealing with this major health problem.

The pandemic of these chronic diseases seems to be linked to a combination of several factors: a "western diet," physical inactivity and genetic and epigenetic factors.

The research to combat these pathologies initially focused on food intake imbalances, both quantitative and qualitative (in particular a high consumption of saturated lipids, fructose and carbohydrates), associated or not with a sedentary lifestyle, which lead to weight gain. However, it was found that everyone is not equal before the same food intake and research has been conducted to assess the impact of genetics and epigenetics on weight gain. This research has shown that only a very small fraction of the problems of excess weight and obesity were attributed in a direct way to genetics. On the other hand, epigenetic results have revealed an interest in the microbiome, which seems to play an important role in many chronic diseases, particularly obesity and cardiometabolic diseases. In particular, it has been found that quantitative dysbiosis but above all functional intestinal dysbiosis can lead to an increase in the absorption and storage of energy in the form of fat, with an equal amount of food intake. This functional dysbiosis is due to the disappearance or marginalization of certain bacteria that have a positive influence on the health of the host. Most of these bacteria are inheritable; this explains the existence of bloodlines of skinny or fat individuals, or the existence of obese individuals who never have metabolic disorders, particularly in the blood glucose and lipids, because they do not have functional intestinal dysbiosis due to the fact that the genes of the host do not undergo mutation.

Indeed, if the existence of a microbiome/brain interaction was the first step in understanding the action of the microbiome, particularly in the context of excess weight through receptors of satiety in particular, the most important discovery was the one of the heritability of bacteria. This notion of heritability was demonstrated by the study of cohorts of monozygotic twins (Goodrich "*Genetic determinant of the gut microbiome in UK twins*," CellPress 2016), and gave an explanation for the transmission of obesity or of certain chronic diseases. Thus, in the context of obesity and cardiovascular diseases, it was discovered that gene variations were directly related to the visceral fat, explaining the epidemics of obesity and metabolic syndrome, in particular diabetes and cardiovascular diseases, a fact that is true in both developed countries and emerging countries such as China and South American countries. This new notion of epigenetics has revolutionized the understanding of many chronic diseases and allows considering new treatments thanks to the bacteria that can compensate genetic changes. This is all the more important as it is now proven that the epigenetics of mother and father can be transmitted to children, especially in obesity. Another object of the invention is therefore to propose a solution for controlling, in particular, excess weight, obesity, cardiometabolic diseases and inflammatory bowel diseases by acting on the intestinal microbiome and, in particular, on inheritable bacteria. The microbiome is a set of microorganisms (bacteria, archaea, viruses and eukaryotes grouped into domains) that are specific to each individual. These microorganisms are found on the skin, in the mouth and in the largest number in the digestive system, which has about 3.3 million of them. This microbiome thus contains a number of genes one hundred and fifty times greater than that of the human genome.

The different classification levels of the bacteria are: domain, phylum, class, order, family, genus, species and strain. The bacteria are also identifiable and can be characterized by OTUs (Operational Taxonomic Units), an OTU corresponding to a grouping of bacteria strains of the same species whose 16S rRNA sequences have a similarity of over 97%.

Several methods currently exist to know and analyze the bacteria constituting the intestinal microbiome:
  cultivation: this technique is limited because 80% of the microbiome is not cultivated (currently, only one thousand species are cultivated because of difficulties in practicing this cultivation);
  biological marking using 16S rRNA as a marker;
  sequencing of OTU either by the Sanger method or by pyrosequencing of the 16S rRNA;
  imprint by electrophoresis, polymorphism and ribosomal;
  DNA chips;
  the FISH and qPCR methods with amplification of a group;
  shotgun metagenomic analysis;
  meta-analysis with metagenomics (composition and function of all genes), metaproteomics (protein analysis), metabolomics (metabolic profile) and metatranscriptomics (RNA).

However, currently, among the millions of bacteria constituting the microbiome, very few (about one thousand) are defined, characterized and cultivated.

Each individual has his own microbiome that comes from his history and his roots, but there are species common to many individuals. In particular, it is known that over 85% of the species are common between Europe, the United States and Japan.

Moreover, the intestinal microbiome is not homogeneous. It varies in quantity and quality when it comes to the stomach, the duodenum, the jejunum, the ileum and finally the colon, where there is the greatest number of anaerobic bacteria. It is also known that certain bacteria are found in the mucus that lines the intestinal wall.

In addition, the immune system, the genetic system and the neurotransmitters (particularly those linking the intestine and the brain) influence the microbiome, making its study even more complex.

It is therefore a particularly delicate domain because of its complexity and the number of inter-reacting factors and it is impossible today to establish a standard microbiome of good health.

We know that the diversity as well as the richness of the microbiome decreases in case of excess weight and obesity (61% of obese individuals have a low number of genera). Research has been conducted on the correlation between certain phyla (including firmicutes, bacteriodetes, proteobacteria and actinobacteria) and excess weight and/or obesity. A relationship in the firmicutes-bacteriodetes ratio has been described as increasing with body mass index (BMI), but with the replication of studies, some scientists have reversed this judgment by demonstrating the opposite. Thus, staying at the level of large groups such as phyla does not provide a solution to combat excess weight and/or obesity and/or chronic metabolic diseases. Research has focused on lower levels of bacterial classification, at the level of families, genera, species and even strains.

Numerous studies have been carried out in the families of bacteria, but, here again, no satisfactory results have been obtained. Indeed, a family can contain dozens of species and even more strains, without the possibility of knowing which bacterium or bacteria is active. In addition, some families may harbor hazardous species alongside beneficial species.

Recent studies have been carried out on species likely to influence weight loss by their increase in the microbiome, namely *Akkermansia muciniphila, Methanobrevibacter smithii, Faecalibacterium prausnitzii, Bifidobacterium longum, Roseburia intestinalis, Eubacterium rectale* and *Christensenella minuta*. However, the studies were carried out only on the mouse, which does not suggest any activity on humans. Mouse studies are unreliable because these animals have a different microbiome from humans and mice with humanized microbiome lose their natural reactions on metabolic markers.

As to cardiometabolic diseases such as diabetes, it has been shown that there may be a significant decline in Clostridiales and an increase in Bacteriodetes in vitro or in animals, as well as a decrease in *Roseburia intestinalis* and *Faecalibacterium pransnitzii*, which are thought to regulate glucose and blood sugar through the permeability of the intestinal barrier, but, here again, these findings do not allow a satisfactory solution to fight against excess weight, obesity and the resulting cardiometabolic diseases because of the excessive number of different bacteria.

Three types of bacterial therapies acting on the microbiome have been proposed to date. The first was to use prebiotics to increase all of the bacteria in order to compensate for the decrease induced by obesity. However, this solution is at best a lure and at worst a danger by increasing the unwanted bacteria which is the natural tendency of the microbiome in dysbiosis. Selective growth was also investigated in vitro by crossing selected food on selected strain but this did not work in humans.

The second consisted in using probiotics as "food" for the development of selected bacteria. This solution is not satisfactory either because the developed probiotics have been limited to the food bacteria which are used in the first part of the intestine, whereas the metabolically interesting bacteria are in the colon and nested in the mucus. Moreover, it is difficult to demonstrate an action on humans in the long term because their activity is highly random. Finally, the third solution proposed is the fecal implantation of bacteria of normal or lean individuals to obese people using a technique that works on mice. This technique has the disadvantage of trying to implant foreign strains which can be rejected and there is a possible transmission of carcinogenic signals according to the fears expressed by oncologists. There is therefore no therapeutic solution acting on the microbiome that is satisfactory for humans who are overweight, obese and/or suffer from cardiometabolic diseases and/or inflammatory bowel diseases.

SUMMARY

The aim of the invention is thus to meet this need by proposing the use of new specific bacteria which act in a particularly effective way to combat excess weight, obesity, cardiometabolic diseases and inflammatory bowel diseases.

To this end, the invention relates to the use of specific bacteria, selected and harvested from the microbiome of overweight or obese individuals having a metabolic syndrome. In particular, the invention relates to inheritable, Gram-negative, strictly anaerobic and commensal bacteria of the family *Christensenellaceae* belonging to an OTU characterized by a 16S rRNA sequence SEQ ID NO:1 or to an OTU characterized by a 16S rRNA sequence SEQ ID NO:2.

Bacteria of the family *Christensenellaceae*, in particular of the genus *Christensenella*, have already been studied, in particular in the application of US Pat. Publication No. 2017/04298. This is particularly true of *Christensenella minuta*, and the unpatented *Christensenella massiliensis* and *Christensenella timonensis*. It is also known that overweight or obese individuals with dysbiosis in inheritable bacteria of the family *Christensenellaceae* demonstrate a variation rs74331972 of their gene FIHT and a variation rs 1433723 of their gene TDRG1 (Beaumont "*Christensenella, heridity and visceral fat inheritable components*," Genome biology 2016).

However, not all bacteria of the family *Christensenellaceae* play a role in excess weight, obesity and/or cardiometabolic and/or inflammatory diseases, and none of the aforementioned bacteria has demonstrated a direct link with these pathologies in humans. The bacteria according to the invention are far removed (see phylogenetic tree in FIG. 1) from those already described for their use in the fight against excess weight, obesity, cardiometabolic diseases and/or inflammatory bowel diseases.

Advantageously, it was extensively demonstrated that the bacteria according to the invention are appreciably efficient against excess weight, obesity, cardiometabolic diseases and inflammatory bowel diseases in humans, in particular by reducing, on the one hand, the visceral fat of an individual and, on the other hand, the intestinal permeability. They were selected, specifically, from a population of overweight or obese people with metabolic syndrome and are therefore perfectly adapted for use as an effective drug in humans with great adaptability for implantation in an inflammatory environment.

The invention also relates to compositions comprising at least one of these bacteria.

Other characteristics and advantages of the invention will emerge from the following detailed description of the invention, made in particular with reference to FIG. 1 which illustrates the phylogenetic tree of the bacteria according to the invention.

BRIEF DESCRIPTION OF THE DRAWINGS

FIG. 1 is a schematic diagram of the phylogenetic tree of bacteria according to the invention.

DETAILED DESCRIPTION

Definitions

The term "rRNA" means ribosomal ribonucleic acid.

The term "16S rRNA" means the rRNA constituting the small subunit of the prokaryotic ribosomes. In bacteria, their sequence allows identifying and characterizing operational taxonomic units.

The term "obesity" means an excessive concentration of fat mass in the body with an increase in the volume of adipose tissue, which is the tissue containing this fat. Obese adult human beings have a body mass index (BMI) greater than 30.

The term "cardiometabolic disease" means a metabolic and/or cardiovascular disease. These cardiometabolic diseases can be induced by excess weight and/or obesity. These may include pre-diabetes, diabetes, vascular and cardiac diseases, atherosclerosis, hyperlipidemia, hyperglycemia, NASH (Non-Alcoholic Steatohepatitis), NAFLD (Non-Alcoholic Fatty Liver Disease)), infarctions, ictus and hypertension.

The expression "use as medicament" means a use for any curative or preventive effect with regard to human or animal diseases, as well as any use in humans for the purpose of establishing a medical diagnosis or restoring, correcting or modifying their organic functions. Use as medicament within the scope of the present invention includes in particular use as a specific modulator of the microbiome to reconstitute an ecosystem beneficial to the health of the host.

The term "cardiometabolic risk" or "metabolic syndrome" is understood to mean a syndrome which comprises at least three risk factors selected in particular among: waist circumference, blood glucose, HDL cholesterol, triglycerides and blood pressure, and which leads to cardiometabolic diseases.

The term "excess weight" means an excessive concentration of fat mass in the body with an increase in the volume of adipose tissue, which is the tissue containing this fat. Overweight adult human beings have a body mass index (BMI) greater than 25.

The term "fecal transplant" means stools intended to be transplanted into an individual and originating either from the individual himself taken before treatment and implanted after treatment, or from another person deemed to be healthy.

The term "OTU" or "Operational Taxonomic Unit" refers to a grouping of bacteria of the same species whose 16S rRNA sequences have a similarity of more than 97%. Thus, an OTU characterized by an "X" 16S rRNA sequence comprises bacteria with a 16S rRNA sequence having a similarity of more than 97.5% with the sequence "X."

The subject-matter of the invention relates to an inheritable Gram-negative, strictly anaerobic, commensal bacterium of the family *Christensenellaceae* belonging to an OTU characterized by a 16S rRNA sequence SEQ ID NO:1 (referred to as OTU 1 for the present disclosure) or an OTU characterized by a 16S rRNA sequence SEQ ID NO:2 (referred to as OTU 2 for the present disclosure), for use as a medicament. In some embodiments, the bacterium is sporulated. In other embodiments, the bacterium is non-sporulated. In further embodiments, a mixture of sporulated and non-sporulated bacteria is used. The OTU 1 and OTU 2 bacteria are commensal and heritable bacteria present in human intestinal mucus. They preferably have a diameter of 0.5 µm.

They may be especially cultivated at a pH of between 7 and 8 under strict anaerobic conditions at a temperature of 37° C. for 4 days on a yeast with a feeder glucose supplementation.

They are small producers of short chain fatty acids, in particular acetic acid, isobutyrate and isovalerate.

The 16S rRNA sequences that specifically, and with certainty, identify these bacteria are far removed from the 16S rRNA sequences of known bacteria of the same family and genus such as *Christensenella minuta, Christensenella massiliensis, Christensenella timonensis*. They are below 90% of *Christensenella minuta* in the phylogenetic tree (see FIG. 1) and are well-defined.

The bacteria according to the invention can be harvested and selected from the intestinal microbiome of a population of overweight or obese individuals with metabolic syndrome. They are correlated with the improvement of many factors characteristic of excess weight, obesity, cardiometabolic diseases or inflammatory bowel diseases, and, in particular, with a decrease in visceral fat. The bacteria according to the invention can be harvested, in particular, by taking fecal matter, in particular fecal matter from an overweight or obese individual in a metabolic syndrome whose genes FIHT and TDRG1 genes have not undergone genetic variation, and, more precisely, whose genes FIHT has not undergone a variation rs74331972 and whose gene TDRG1 has not undergone a variation rs 1433723.

The bacteria useful according to the invention can be administered to humans by any suitable mode of administration, in particular orally or rectally.

They are particularly useful in the treatment of excess weight, obesity and/or in the treatment of cardiometabolic diseases and/or inflammatory bowel diseases, particularly cardiometabolic and/or inflammatory bowel diseases induced by excess weight and obesity. Advantageously, the bacteria according to the invention are in particular capable of:

reducing the weight and/or reducing visceral fat and subcutaneous fat and/or preserving lean mass and/or reducing liver fat and block fibrosis of the liver and/or reducing waist circumference and/or normalizing blood pressure and/or reducing the inflammation of the intestinal barrier, muscle or adipose organs and tissues, in particular the colon and/or reducing the permeability of the intestinal barrier by acting on the reconstitution of the mucus, closing the tight junctions, reactivating the hormonal receptors such as, in particular, TLR4, GPL2, CCK and/or regulating HDL, LDL and total cholesterol and/or regulating triglycerides and/or reducing blood glucose and/or post-prandial glucose and/or insulin resistance and/or insulin sensitivity and/or reducing intestinal inflammation, especially in inflammatory bowel diseases and in particular Crohn's disease (Crohn's disease being linked to the metabolic syndrome and therefore to the same microbiome).

These various factors are characteristics or consequences of cardiometabolic diseases or inflammatory bowel diseases, in particular in overweight or obese individuals, so that the action on these factors by the bacteria according to the invention allows controlling excess weight, obesity, cardiometabolic diseases and inflammatory bowel diseases.

The bacteria according to the invention are therefore particularly useful in the treatment of excess weight, obesity, metabolic syndrome, pre-diabetes, diabetes, vascular and cardiac diseases, atherosclerosis, hyperlipidemia, hyperglycemia, NASH (Non-Alcoholic Steatohepatitis), NAFLD (Non-Alcoholic Fatty Liver Disease) and/or IBD (Inflammatory Bowel Disease), in particular Crohn's disease.

Advantageously, the invention allows acting on the reconstitution of the mucus, the epithelium and the increase of the impermeability of the intestinal barrier for the modulation of the tight junctions in order to reduce endotoxemia and the blood translocation of bacteria and lipopolysaccharides (LPS) endotoxins. Indeed, overweight and obese individuals and those with cardiometabolic diseases and/or inflammatory bowel disease have a degraded and thin mucus that is poorly renewed. In addition, the inflamed epithelium is deficient with very open tight junctions that allow bacteria and LPS to penetrate. This phenomenon is due to the inflammation of the intestine and causes a low grade chronic inflammation in the body.

The useful bacteria according to the invention are particularly suitable for persons with a BMI greater than 25 and, in particular, greater than 30, and/or persons suffering from hypertriglycemia.

Advantageously, the use of OTU 1 and/or OTU 2 bacteria makes it possible to increase the efficient bacterial population of the family *Christensenellaceae* without increasing potentially dangerous bacteria such as *Catabacter hongkongensis* of the same order and close to *Christensenella minuta*.

The bacteria according to the invention can be used in conjunction with nutritional rebalancing and/or caloric restriction. Nutritional rebalancing may include, in particular, the removal from the diet of the nutrients that are deleterious to the microbiome such as fructose and trans fatty acids. The caloric restriction is preferably light, about 600 kcal/day. It notably allows modulating glucose homeostasis, protein turnover and lipogenesis.

The bacteria according to the invention can be used at a daily unit dose of $10^4$ to $10^{12}$ (in number of bacteria), preferably between $10^8$ and $10^{12}$.

Preferably, the bacteria according to the invention are administered on a daily to a weekly basis. Such a frequency makes it possible to keep a sufficient colony of bacteria according to the invention in the microbiome and to avoid that the mortality of the bacteria be greater than the growing bacteria.

Determining the frequency is based on several criteria, in particular the importance of the symptom to be treated, the importance of the visceral fat to be lost, the importance of hyperglycemia or hypertriglyceremia or the frequency of diarrhea.

The treatment will last until the desired result is achieved; a maintenance treatment may be recommended for cases where the implantation of the bacteria has been long.

A stool analysis or a mucus sampling to check the OTU 1 and/or OTU 2 content is not mandatory for all patients at the start of treatment because it is a heritable bacterium linked directly to the fat visceral. However, it may be necessary for patients with very high BMI or high inflammation (CRP us). Similarly, if after several months of treatment the result according to the desired effects (decrease in waist circumference, weight loss, decrease in hyperglycemia, etc.) is not achieved, it is preferable to carry out a stool analysis to verify that the bacteria have nested well or if strongly disturbed genetic or epigenetic factors require the use of a greater frequency of administration than that originally intended.

In all cases, a stool analysis or direct mucus sampling is preferable after one year of the end of treatment.

The advantage of bacteria of the family *Christensenellaceae* is to have a good correlation between the presence of these bacteria in the stool and in the mucus, which does not require taking samples by endoscopy in the colon.

Advantageously, the bacteria according to the invention can be used in the context of a personalized medicament. Indeed, it is possible to adapt the treatment to the genetics of the patient to know to what extent he will respond to the treatment and what the dose to be used should be. In the context of the inheritable bacteria of the family of *Christensenellaceae*, the genes which undergo a variation are known: these are FHIT with the variation rs 74331972 and TDRG1 with the variation rs 1433723. It is thus possible to use genetic analysis of the host in parallel with the genetic analysis of the microbiome to fully customize the treatment of the patient in severe cases with possible resistance to treatment in order to adjust the dose to be administered.

The bacteria according to the invention may be used alone directly, but they are preferentially used within a composition.

The object of the invention is therefore also a composition comprising at least one OTU 1 or at least one OTU 2, that is to say at least one inheritable, Gram-negative, strictly anaerobic, commensal bacterium of the family *Christensenellaceae* belonging to an OTU characterized by a 16S rRNA sequence SEQ ID NO:1 or at least one inheritable, Gram-negative, strictly anaerobic, commensal bacterium of the family *Christensenellaceae* belonging to an OTU characterized by a 16S rRNA sequence SEQ ID NO:2.

The composition also comprises excipients, known to those skilled in the art and conventionally used in the pharmaceutical industry, to be adapted as a function of the galenic form of the composition.

According to a particularly suitable embodiment, the composition according to the invention comprises the combination of:

at least one inheritable, Gram-negative, strictly anaerobic, commensal bacterium of the family *Christensenellaceae* belonging to an OTU characterized by a 16S rRNA sequence SEQ ID NO:1 (OTU 1) and at least one inheritable, Gram-negative, strictly anaerobic, commensal bacterium of the family *Christensenellaceae* belonging to an OTU characterized by a 16S rRNA sequence SEQ ID NO:2 (OTU 2).

Advantageously, the combination of the bacteria according to the invention belonging to OTU 1 and of the bacteria according to the invention belonging to OTU 2 allows obtaining a greater effect on the desired therapeutic applications.

The OTU 1 and/or OTU 2 bacteria may also be associated with other bacteria in the composition.

The composition may also comprise at least one inheritable, Gram-negative, strictly anaerobic, commensal bacterium of the family *Christensenellaceae* belonging to an OTU referred to as OTU 3 for the present disclosure, characterized by a sequence of 16S rRNA SEQ ID NO:3 and/or at least one bacterium belonging to an OTU (referred to as OTU 4 for the present disclosure) characterized by a 16S rRNA sequence SEQ ID NO:4 and/or at least one bacterium belonging to an OTU (referred to as OTU 5 for the present disclosure) characterized by a 16S rRNA sequence SEQ ID NO:5 and/or at least one bacterium belonging to an OTU (referred to as OTU 6 for the present disclosure) characterized by a 16S rRNA sequence SEQ ID NO:6 and/or at least one bacterium belonging to an OTU (referred to as OTU 7 for the present disclosure) characterized by a 16S rRNA sequence SEQ ID NO:7 and/or at least one bacterium belonging to an OTU (referred to as OTU 8 for the present disclosure) characterized by a 16S rRNA sequence SEQ ID NO:8 and/or at least one bacterium belonging to an OTU (referred to as OTU 9 for the present disclosure) characterized by a 16S rRNA sequence SEQ ID NO:9 and/or at least one bacterium belonging to an OTU (referred to as OTU 10 for the present disclosure) characterized by a 16S rRNA sequence SEQ ID NO:10 and/or at least one bacterium belonging to an OTU (referred to as OTU 11 for the present disclosure) characterized by a 16S rRNA sequence SEQ ID NO:11 and/or at least one bacterium belonging to an OTU (referred to as OTU 12 for the present disclosure) characterized by a 16S rRNA sequence SEQ ID NO:12 and/or at least one bacterium belonging to an OTU (referred to as OTU 13 for the present disclosure) characterized by a 16S rRNA sequence SEQ ID NO:13 and/or at least one bacterium belonging to an OTU (referred to as OTU 14 for the present disclosure) characterized by a 16S rRNA sequence SEQ ID NO:14 and/or at least one bacterium belonging to an OTU (referred to as OTU 15 for the present disclosure) characterized by a 16S rRNA sequence SEQ ID NO:15.

These bacteria are capable of acting on the same factors as the useful bacteria according to the invention, but are difficult to use alone because they are less frequent in the microbiome and thus their implantation is more random. On the other hand, their use in combination with the bacteria according to the invention allows improving the effectiveness of the latter and reinforces the ecosystem of the *Christensenellaceae*. They can be selected in the same manner as OTU 1 and/or OTU 2.

The composition according to the invention may also comprise one or more methanogenic bacteria of the family Methanobacteriaceae, of the genus *Methanobacterium* and/or *Methanobrevibacter* and/or *Methanosphaera* and/or *Methanothermobacter*, in particular *Methanothermobacter smithii*. The methanogens facilitate the implantation of the *Christensenellaceae*, especially in obese or diabetic patients, but should be used with caution in inflammatory bowel diseases.

It may also comprise one or more bacteria of the following species, genus or order: *Marvinbryantia formatexigens* and/or *Bacteroides thetaiotaomicron* and/or *Akkermansia muciniphila* and/or *Faecalibacterium prausnitzii* and/or *Clostridium thermocellum* and/or Dehalobacteriaceae and/or *Oscillospira* and/or Mogibacteriaceae and/or Ruminococcaceae and/or *Ruminococcus* and/or Lachinospiraceae and/or *Lachinospira* and/or Bacteroidaceae and/or Rikenellaceae and/or *Clostridium* and/or Clostridiales IV and XIVa and/or *Eubacterium hallii*. All of these bacteria may be bacteria of the known strains currently cultivated, or may be new strains, in particular strains harvested from the fecal matter of an overweight or obese individual in metabolic syndrome in order to obtain strains resistant to inflammation characteristic of overweight or obese individuals. These bacteria are known to have an influence on the regulation of weight in mice even if most are not inheritable therefore with an unknown mode of action. The most plausible scientific hypothesis is that they reinforce the ecosystem of the family *Christensenellaceae*.

The useful bacteria according to the invention may also be used in combination with at least one other bacterium selected from *Christensenella massiliensis*, *Christensenella timonensis* and *Christensenella minuta*. Here again, these bacteria can be harvested from the fecal matter of an overweight or obese individual in metabolic syndrome in order to obtain strains resistant to inflammation characteristic of overweight or obese individuals. These bacteria are of the family *Christensenellaceae* with a less effective action in clinical experiments on obese patients with a cardiometabolic risk but they allow creating both a synergy and above all a strengthening of the ecosystem of the bacteria of the invention.

The compositions according to the invention may also comprise other constituents, in particular at least one amino acid and/or at least one peptide. These may in particular be threonine, leucine, serine, proline, alanine, glycine, glutamine, glutamic acid and tryptophan and/or at least one peptide containing at least one of these amino acids. According to a variant, these amino acids can be administered in parallel with the bacteria according to the invention, but in an independent composition. The amount of each of the amino acids or biopeptides is preferably comprised between 500 mg and 1 g per day.

The presence of amino acid(s) or peptide(s) in addition to the useful bacteria according to the invention allows, in particular, to reinforce the intestinal mucus and to restore the intestinal barrier by reducing its permeability. These two factors are characteristic of obese people and cardiometabolic patients whose mucus is thinner, preventing the commensal bacteria from developing like the bacteria according to the invention, the tight junctions being widely open allowing endotoxemia which causes chronic inflammation of the body. The compositions according to the invention may also be associated with at least one probiotic and/or at least one prebiotic. They may be, for example, oligosaccharides, in particular RS4 for prebiotics, or lactic ferments for probiotics. Probiotics improve the quantitative dysbiosis and general health of the microbiota. Prebiotics allow increasing the feeding of the bacteria according to the invention which have been implanted. Preferably, the prebiotics and/or the probiotics are administered at the beginning of the treatment along with the bacteria according to the invention.

The bacteria according to the invention are preferably used while alive, but could be also pasteurized or it could be a part of the bacteria as the membrane or its metabolites as proteins, peptides or short chain fatty acids.

The bacteria useful according to the invention and the compositions including them may be in any form. Preferably, the bacteria and/or the composition are in lyophilized form. Preferably, the compositions according to the invention are in the form of powder, microencapsulated powder, capsule, capsugel, tablet or fecal transplant.

According to a particularly suitable variant, the compositions according to the invention are in a gastro-resistant form, in particular in a gastro-resistant form intended to be absorbed in the intestine, particularly at the level of the terminal ileum or the entrance to the colon.

The compositions according to the invention are produced by simple mixing of the constituents and/or by conventional methods known to those skilled in the art and adapted to the desired galenic forms.

The compositions according to the invention can be used for all therapeutic applications, in particular all therapeutic applications of the useful bacteria according to the invention, as described in the present application.

Preferably, the compositions according to the invention are used at a daily unit dose for each bacterium present in the composition (OTU 1, OTU 2 and other bacteria possibly present) from $10^4$ to $10^{12}$. It is possible to adapt the dosage of the bacteria present in the composition according to several criteria, in particular as a function of the quantity of said bacteria found in the stools taken from the persons to be treated.

The bacteria and compositions according to the invention can be given to adults as well as to the elderly, children and adolescents. The dosage may be the same for all patients, regardless of age.

Advantageously, the invention allows reducing the great number of therapeutic failures stemming either from abandoning the treatment in progress, or most often at the beginning, or from gaining weight again after a few months and with a greater amount of visceral fat mass than before, or from the persistence of chronic cardiometabolic and/or inflammatory diseases and their acute manifestations.

The invention is now illustrated by examples of compositions according to the invention and by a clinical study demonstrating the efficacy and the interest of the bacteria according to the invention.

EXAMPLES OF COMPOSITIONS ACCORDING TO THE INVENTION

Example 1

This example of composition according to the invention is a composition in lyophilized form comprising OTU 1 (comprising SEQ ID NO. 1) and at least one suitable excipient.

Example 2

This example of composition according to the invention is a composition in lyophilized form comprising OTU 2 (comprising SEQ ID NO. 2) and at least one suitable excipient.

Example 3

This example of composition according to the invention is a composition in lyophilized form comprising OTU 1 (comprising SEQ ID NO. 1) and OTU 2 (comprising SEQ ID NO. 2) and at least one suitable excipient.

Example 4

This example of composition according to the invention is a composition in lyophilized form comprising OTU 1 (comprising SEQ ID NO. 1), OTU 2 (comprising SEQ ID NO. 2), OTU 3 (comprising SEQ ID NO. 3), OTU 4 (comprising SEQ ID NO. 4), OTU 5 (comprising SEQ ID NO. 5), OTU 6 (comprising SEQ ID NO. 6), OTU 7 (comprising SEQ ID NO. 7), I OTU 8 (comprising SEQ ID NO. 8), OTU 9 (comprising SEQ ID NO. 9), OTU 10 (comprising SEQ ID NO. 10), OTU 11 (comprising SEQ ID NO. 11), OTU 12 (comprising SEQ ID NO. 12), OTU 13 (comprising SEQ ID NO. 13), OTU14 (comprising SEQ ID NO. 14) and OTU15 (comprising SEQ ID NO. 15) and at least one suitable excipient.

Example 5

This exemplary composition according to the invention is a composition in lyophilized form comprising OTU 1 (comprising SEQ ID NO. 1), OTU 2 (comprising SEQ ID NO. 2) and *Akkermansia muciniphila* and at least one suitable excipient.

Example 6

This exemplary composition according to the invention is a composition in lyophilized form comprising OTU 1 (comprising SEQ ID NO. 1), OTU 2 (comprising SEQ ID NO. 2) and *Methanobrevibacter smithii* and at least one suitable excipient.

Example 7

This example of composition according to the invention is a composition in lyophilized form comprising OTU 1 (comprising SEQ ID NO. 1), OTU 2 (comprising SEQ ID NO. 2), *Christensenella massiliensis, Christensenella timonensis* and *Christensenella minuta* and at least one suitable excipient.

Example 8

This example of composition according to the invention is a composition in lyophilized form comprising OTU 1 (comprising SEQ ID NO. 1), OTU 2 (comprising SEQ ID NO. 2), *Faecalibacterium prausnitzii, Oscillospira* and *Lachinospira* and at least one suitable excipient.

Example 9

This example of composition according to the invention is a composition in lyophilized form comprising OTU 1 (comprising SEQ ID NO. 1), OTU 2 (comprising SEQ ID NO. 2), *Eubacterium Hallii*.

Example 10

This example of composition according to the invention is a composition in lyophilized form comprising OTU 1 (comprising SEQ ID NO. 1), OTU 2 (comprising SEQ ID NO. 2), Clostridiales IV and/or Clostridiales XIVa.

Evaluation of the Effect of the Invention

An interventional clinical study was carried out in France on a population of 107 obese or overweight individuals in metabolic syndrome with abdominal obesity (waist circumference greater than 86 cm for women and 94 cm for men) and two other risk factors of the metabolic syndrome.

A product known to fight excess weight, obesity and metabolic syndrome was administered with a 600 kcal caloric restriction for a duration of 12 weeks.

Patients' stools were collected at the beginning and the end of the study after 12 weeks to detect the effects on the correlations between the bacteria present in the stool and the evolution of the clinical signs. The main criterion of the metabolic syndrome evolution was the visceral fat mass measured by CT Scan and the weight as a secondary criterion.

The determination and characterization of the bacteria was carried out by analysis of the 16S rRNA, confirmed by qPCR and a shotgun metagenomic.

It was found that only 286 OTUs were significantly related to the loss of visceral fat ($p=0.002$) and weight in men. These bacteria belong to the order Clostridiales and the family *Christensenellaceae*. Among these 286 OTUs, 15 of them had a sufficient representativeness in the patients studied and a positive correlation with the loss of visceral fat. It was also noted that the action of these bacteria was greater on patients with initial hypertriglyceremia. These OTUs are OTUs 1 to 15, as described in the present application.

The starting amount of these OTUs and their evolution after treatment is presented in Table 1 below.

TABLE 1

| Bacteria | Number of modulated patients | % of the number of patients | Starting amount of bacteria (%) | Evolution (multiplied by) | p student | Δ% Weight | P student | Δ% Visceral fat | P Student |
|---|---|---|---|---|---|---|---|---|---|
| Total population | 107 | — | — | — | — | | | -9.4 | 0.0000 |
| OTU1 | 21 | 41 | 0.00043 | 5.88 | 0.0007 | -4.8 | 0.0000 | -12.8 | 0.0003 |
| OTU 2 | 19 | 37 | 0.00013 | 2.97 | 0.0002 | -4.8 | 0.0000 | -15.4 | 0.0003 |
| OTU 3 | 10 | 20 | 0.00198 | 2.16 | 0.0043 | -5.1 | 0.0008 | -19.5 | 0.0093 |
| OTU4 | 10 | 20 | 0.00019 | 3.39 | 0.0354 | -5.1 | 0.0019 | -16.4 | 0.0136 |
| OTU 5 | 10 | 20 | 0.00001 | 54.78 | 0.2932 | -4.2 | 0.0125 | -17.7 | 0.0035 |
| OTU 6 | 12 | 24 | 0.00006 | 5.68 | 0.0020 | -4.4 | 0.00325 | -12.8 | 0.0043 |
| OTU 7 | 15 | 29 | 0.00005 | 4.96 | 0.0000 | -5.1 | 0.0004 | -12.9 | 0.0092 |
| OTU 8 | 4 | 8 | 0.00055 | 2.84 | 0.1627 | -7.4 | 0.0510 | -27.0 | 0.0655 |
| OTU 9 | 7 | 14 | 0.00005 | 11.14 | 0.0247 | -6.0 | 0.0056 | -15.4 | 0.0797 |
| OTU 10 | 4 | 8 | 0.00018 | 5.23 | 0.2216 | -5.1 | 0.0305 | -14.1 | 0.0301 |
| OTU 11 | 6 | 12 | 0.00045 | 1.52 | 0.0122 | -4.2 | 0.0018 | -11.2 | 0.0737 |
| OTU 12 | 3 | 6 | 0.00035 | 4.50 | 0.2345 | -7.0 | 0.0916 | -22.4 | 0.2086 |
| OTU 13 | 5 | 10 | 0.00052 | 4.51 | 0.2760 | -6.1 | 0.0397 | -19.9 | 0.0127 |
| OTU 14 | 3 | 6 | 0.00025 | 10.04 | 0.3264 | -3.2 | 0.0147 | -9.7 | 0.0567 |
| OTU 15 | 2 | 4 | 0.00073 | 5.70 | 0.4820 | -4.2 | 0.0941 | -6.8 | 0.2463 |

In addition, the precise action of each of OTU 1 and OTU 2 was evaluated in terms of the results of the study population. The results are shown in Table 2 below.

TABLE 2

| Bacteria | Results 16S baseline Starting quantity | Evolution X times | Δ% Weight evolution | % vs. Evolution of total population | Δ% Evolution of visceral fat mass | % vs. MGV evolution of the total population |
|---|---|---|---|---|---|---|
| Total population | 107 | | -3.6 | | -9.4 | |
| Study population without OTU 1 and OTU 2 bacteria | | | -3.4 | -6% | -8.9 | -5% |
| OTU 1 | 0.00043 | 5.9 | -4.8 | +33% | -12.8 | +36% |
| OTU 2 | 0.00013 | 3.0 | -4.8 | +33% | -15.4 | +64% |
| Total of 2 OTU 1 and OTU 2 bacteria | 0.00042 | 5.1 | -4.8 | +33% | -13.4 | +43% |

The increase of the bacteria according to the invention in the microbiome is directly linked to a reduction in the weight and the fat mass in humans. The bacteria according to the invention therefore play a primary role in the fight against excess weight, obesity, cardiometabolic diseases and inflammatory diseases, in particular related to visceral fat, and can be used for this purpose.

It was also found that the best results are obtained with individuals having a BMI greater than 30.

It is also noted that the OTUs 1 and 2 according to the invention were already present in sufficient quantity to be detected and individualized in the study patients despite their excess weight or obesity and metabolic syndrome. The presence of these bacteria in a highly inflammatory environment means that they have become resistant to inflammation and that the two genes FHIT and TDRG1 have partially resisted the epigenetics of the diet or the epigenetic transmission of the parents.

| Sequences |
|---|
| OTU 1 16S rRNA (SEQ ID NO. 1) |

```
OTU 1 16S rRNA (SEQ ID NO. 1)
tggggaatat tgggcaatgg gcgaaagcct tacccagcaa cgccgcgtga gggaagaagg    60
ttttcggatt gtaaacctct gtcctggggg acgaaggaag tgacggtacc ccgggaggaa   120
gccccggcta actacgtgcc agcagccgcg gtaatacgta gggggcgagc gttgtccgga   180
attattgggc gtaaagggcg cgtagacggc tgtgtaagtt ataggtgaaa gcccaacttt   240
caaggttgga actgcctgta atactgcatg gcttgagtgc aggagaggga agcggaattc   300
ctagtgtagc ggtgaaatgc gtagatatta ggaggaacac cagtggcgaa ggcggctttc   360
tggactgtaa ctgacgttga ggcgcgaaag cgtggggagc aaacagg               407

OTU 2 16S rRNA (SEQ ID NO. 2)
ggggaatat tggcaatgg gggaaaccct gacccagcaa cgccgcgtga aggaagaagg    60
ccttcgggtt gtaaacttct gtgacagggg acgaaggaag tgacggtacc ctgagaggaa   120
gctccggcaa actacgtgcc agcagccgcg gtaatacgta gggagcgagc gttgtccgga   180
attactgggc gtaaagggcg cgtaggcggt agatcaagtc gcatgtgaaa tacccgggct   240
caacctgggg ggtgcatgcg aaactggaat acttgagtgc ggtagaggaa agtggaattc   300
ctagtgtagc ggtgaaatgc gtagatatta ggaggaacac cagtggcgaa ggcgactttc   360
tgggccgtaa ctgacgctga ggcgcgaaag cgtggggagc aaacagg               407

OTU 3 16S rRNA (SEQ ID NO. 3)
tggggaatat tgggcaatgg gcgcaagcct gacccagcaa cgccgcgtga gggaagaagg    60
ttttcggatt gtaaacctct gtcgcagaag acgaaggaag tgacggtatt ctgtgaggaa   120
gccccggcta actacgtgcc agcagccgcg gtaatacgta gggggcgagc gttgtccgga   180
attactgggc gtaaagggag cgtaggcggt ctgataagtt ggatgtgaaa tacccgggct   240
taacttgggg ggtgcatcca atactgttgg actagagtac aggagaggaa agcggaattc   300
ctagtgtagc ggtgaaatgc atagatatta ggaggaacat cggtggcgaa ggcggctttc   360
tggactgcaa ctgacgctga ggctcgaaag cgtggggagc aaacagg               407

OTU 4 16S rRNA (SEQ ID NO. 4)
tagggaatat tggacaatgg ggggaaccct gatccagcaa cgccgcgtga aggaagaagg    60
tcttcggatt gtaaacttat gttgtcgggg acgaagaaag acggtacccg acgaggaagc   120
cccggctaac tacgtgccag cagccgcggt aatacgtagg gggcgagcgt tgtccggaat   180
tactgggcgt aaaggcgcg taggcggcat attaagttag atgtgaaatc cccgggctta   240
acctgggtgt tgcatttaaa actgataagc ttgagtgcag gagagggaag cggaattcct   300
agtgtagcgg tggaatgcgt agatattagg aggaacacca gtggcgaagg cggctttctg   360
gactgtaact gacgctgagg cgcgagagcg tggggagcaa acaggcc               407

OTU 5 16S rRNA (SEQ ID NO. 5)
tagggaatat tgggcaatgg gcgcaagcct gacccagcaa cgccgcgtga gggaagaagg    60
ttttcggatt gtaaacctct gtcctatgtg acgaaggaag tgacggtagc ataggaggaa   120
gccccggcta actacgtgcc agcagccgcg gtaatacgta gggggcgagc gttgtccgga   180
attactgggc gtaaagggtg cgtaggcggt ttggtaagtt ggatgtgaaa tacccgggct   240
taacttgggg gctgcatcca atactgtcgg acttgagtgc aggagaggaa agcggaattc   300
ctagtgtagc ggtgaaatgc gtagatatta ggaggaacac cagtggcgaa ggcggcttgc   360
tggacagtaa ctgacgctga ggcgcgaaag cgtggggagc aaacagg               407

OTU 6 16S rRNA (SEQ ID NO. 6)
tagggaatat tgggcaatgg gcgcaaccct gacccagcaa cgccgcgtga gggaagaagg    60
ttctctggat tgtaaacctc gtcctatgg gacgaagaag tgacggtacc ataggaggaa   120
```

| Sequences |
|---|
| gctccggcta actacgtgcc agcagccgcg gtaatacgta gggagcgagc gttgtccgga 180 |
| attactgggc gtaaagggtg cgtaggcggc ctggtaagtc agatgtgaaa tacccgtgct 240 |
| caacatgggg ggtgcatctg atactgttag gcttgagtgc aggagaggaa agcggaattc 300 |
| ctagtgtagc ggtgaaatgc gtagatatta ggaggaacac cagtggcgaa ggcggctttc 360 |
| tggactgtaa ctgacgctga ggcacgaaag cgtggggagc aaacagg 407 |

OTU 7 16S rRNA (SEQ ID NO. 7)
tggggaatat tgggcaatgg gggcaaccct gacccagcaa cgccgcgtga gggaagaagg 60
ttttcggatt gtaaacctct gtccttgggg acgaagaagt gacggtaccc aaggaggaag 120
ctccggctaa ctacgtgcca gcagccgcgg taatacgtag ggagcgagcg ttgtccggaa 180
ttactgggcg taaagggtgc gtaggcggtt tggtaagtca gatgtgaaat acccgggctt 240
aacccggggg ctgcatctga tactgtcaga cttgagtgca ggagaggaaa gcggaattcc 300
tagtgtagcg gtgaaatgcg tagatattag gaggaacacc agtggcgaag gcggctttct 360
ggactgtaac tgacgctgag gcacgaaagc gtggggagca aacaggg 407

OTU 8 16S rRNA (SEQ ID NO. 8)
tcgggaatat tggacaatgg gggaaaccct gatccagcaa cgccgcgtga aggaagaagg 60
tcttcggatt gtaaacttat gttgtcgggg acgaagaaag acggtacccg acgaggaagc 120
cccggctaac tacgtgccag cagccgcggt aatacgtagg gggcgagcgt tgtccggaat 180
tactgggcgt aaagggcgcg taggcggcca attaagttag atgtgaaatc cccgggctta 240
acctgggtgt tgcatttaaa actgataggc ttgagtgcag gagagggaag cggaattcct 300
agtgtagcgg tggaatgcgt agatattagg aggaacacca gtggcgaagg cggctttctg 360
gactgtaact gacgctgagg cgcgagagcg tggggagcaa acaggcc 407

OTU 9 16S rRNA (SEQ ID NO. 9)
tggggaatat tgggcaatgg gcggaagcct gacccagcaa cgccgcgtga gggaagaagg 60
ttttcggatt gtaaacctct gtcgcagaag acgaaggaag tgacggtatt ctgtgaggaa 120
gccccggcta actacgtgcc agcagccgcg gtaatacgta gggggcgagc gttgtccgga 180
attactgggc gtaaagggtg cgtaggcggt tgcttaagtt ggatgtgaaa tacccgggct 240
taacttgggg ggtgcattca agactgggga actagagtac aggagaggga agcggaattc 300
ctagtgtagc ggtgaaatgc gtagatatta ggaggaacac cggtggcgaa ggcggctttc 360
tggactgaca ctgacgctga ggcacgaaag cgtggggagc aaacagg 407

OTU 10 16S rRNA (SEQ ID NO. 10)
tggggaatat tgggcaatgg gcgcaagcct gacccagcaa cgccgcgtga gggaagaagg 60
ttttcggatc gtaaacctct gttgcagggg acgaggagta gacggtaccc tacgaggaag 120
ctccggctaa ctacgtgcca gcagccgcgg taatacgtag ggagcaagcg ttgtccggaa 180
tgactgggcg taaagggcgc gtaggtggtt ttgtaagtct ggagtgaaac cccgttttc 240
aaggcgggc ctgctttgga gactgcagga cttgagtgat ggagaggata gcggaattcc 300
cggtgtagcg gtgaaatgcg tagagatcgg gaggaacacc agtggcgaag gcggctatct 360
ggacatagac tgacactgag gcgcgaaagc gtggggagca aacaggc 407

OTU 11 16S rRNA (SEQ ID NO. 11)
tggggaatat tgggcaatgg gcgcaagcct gacccagcaa cgccgcgtga gggaagaagg 60
tcttcggatt gtaaacctct gtcgcaaggg acgaaggcgt gacggtacct tgtgaggaag 120
ccccggctaa ctacgtgcca gcagccgcgg taatacgtag ggggcgagcg ttgtccggaa 180

| Sequences |
|---|
| ttactgggcg taaagggtgc gtaggcggtt gcttaagttg gatgtgaaat acccgggctt 240 |
| aacttggggg gtgcattcaa aactgggcga ctagagttca ggagagggaa gcggaattcc 300 |
| tagtgtagcg gtgaaatgcg tagatattag gaggaacacc agtggcgaag gcggctttct 360 |
| ggactataac tgacgctgag gcacgaaagc gtggggagca aacaggc 407 |
| OTU 12 16S rRNA (SEQ ID NO. 12) |
| tggggaatat tgggcaatgg gcgcaaccct gacccagcaa cgccgcgtga gggaagaagg 60 |
| ttttcggatt gtaaacctct gtcgcagaag acgaaggaag tgacggtatt ctgtgaggaa 120 |
| gccccggcta actacgtgcc agcagccgcg gtaatacgta gggggcgagc gttgtccgga 180 |
| attactgggc gtaaagggtg cgtaggcggt taattaagtt ggatgtgaaa ttcccgggct 240 |
| taacttggga gctgcattca aaactggtta actagagttc aggagaggga agcggaattc 300 |
| ctagtgtagc ggtgaaatgc gtagatatta ggaggaacac cagtggcgaa ggcgacttac 360 |
| tggacgaaca ctgacgctga ggcacgaaag cgtggggagc aaacagg 407 |
| OTU 13 16S rRNA (SEQ ID NO. 13) |
| tggggaatat tgggcaatgg gcgcaagcct gacccagcaa cgccgcgtga aggaagaagg 60 |
| tcttcggatt gtaaactttt gtcgccggga acgataatga cggtacccgg taagaaagcc 120 |
| ccggctaact acgtgccagc agccgcggta atacgtaggg ggcgagcgtt gtccggaatt 180 |
| actgggcgta aagggcgcgt aggcggccgg ataagttaga tgtgaaatcc ccgggctcaa 240 |
| cctgggtgtt gcatttaaaa ctgtctggct tgagtgcagg agaggaaagc ggaattccta 300 |
| gtgtagcggt gaaatgcgta gatattagga ggaacatcag tggcgaaggc ggctttctgg 360 |
| actgtaactg acgctgaggc gcgaaagcgt ggggagcaaa caggccc 407 |
| OTU 14 16S rRNA (SEQ ID NO. 14) |
| tggggaatat tgggcaatgg gcgaaagcct gacccagcaa cgccgcgtga gggaagaagg 60 |
| ccttcgggtt gtaaacctct gtccttagtg acgaaggaag tgacggtagc taaggaggaa 120 |
| gccccggcta actacgtgcc agcagccgcg gtaatacgta gggggcgagc gttgtccgga 180 |
| attactgggc gtaaagggtg cgtaggcggt actttaagtt ggatgtgaaa tccccgggct 240 |
| taacctgggg cctgcatcca atactggaga actagagtgc aggagaggga agcggaattc 300 |
| ctagtgtagc ggtgaaatgc gtagatatta ggaagaacac cagtggcgaa ggcggctttc 360 |
| tggactgtaa ctgacgctga ggcacgaaag cgtggggagc aaacagg 407 |
| OTU 15 16S rRNA (SEQ ID NO. 15) |
| tggggaatat tgcgcaatgg gcgcaagcct gacgcagcaa cgccgcgtga gggaagaagg 60 |
| ctttcgggtt gtaaacctct gtccttggtg acgaaggaag tgacggtagc caaggaggaa 120 |
| gccccggcta actacgtgcc agcagccgcg gtaatacgta gggggcgagc gttgtccgga 180 |
| attactgggc gtaaagggtg cgtaggcggt ctattaagtt ggatgtgaaa tccccgggct 240 |
| taacttgggg tctgcatcca atactgggag actagagtgc aggagaggga agcggaattc 300 |
| ctagtgtagc ggtgaaatgc gtagatatta ggaggaacac cagtggcgaa ggcggctttc 360 |
| tggactgtaa ctgacgctga ggcacgaaag cgtggggagc aaacagg 407 |

The invention claimed is:

1. A method of increasing the population of an inheritable, Gram-negative, strictly anaerobic and commensal bacterium of the family *Christensenellaceae* belonging to an OTU (Operational Taxonomic Unit) comprising the 16S rRNA sequence of SEQ ID NO: 1 in the intestinal microbiome of a patient, wherein the method comprises administering to the patient a daily unit dose of $10^4$ to $10^{12}$ of live, inheritable, Gram-negative, strictly anaerobic and commensal bacteria of the family *Christensenellaceae* belonging to the OTU comprising a 16S rRNA sequence having more than 97% similarity to SEQ ID NO: 1, wherein the bacteria are administered orally or rectally.

2. The method of claim 1, wherein said bacteria of the family *Christensenellaceae* comprise the 16S rRNA sequence of SEQ ID NO: 1.

3. The method of claim 1, wherein the patient has excess body weight or obesity.

4. The method of claim 1, wherein the patient has a cardiometabolic disease and/or an inflammatory bowel disease.

5. The method of claim 1, wherein the patient has metabolic syndrome, pre-diabetes, or diabetes.

6. The method of claim 1, wherein the patient has vascular disease, cardiac disease, atherosclerosis, hyperlipidemia, or hyperglycemia.

7. The method of claim 1, wherein the patient has Non-Alcoholic Steatohepatitis (NASH), Non-Alcoholic Fatty Liver Disease (NAFLD) and/or Crohn's disease.

8. The method of claim 1, wherein the patient has hypertriglycemia.

9. The method of claim 1, wherein the patient has a Body Mass Index (BMI) greater than 25.

10. The method of claim 1, wherein the patient has a Body Mass Index (BMI) greater than 30.

11. The method of claim 1, further comprising a balanced diet and/or caloric restriction.

* * * * *

SEQUENCE LISTING

<160> NUMBER OF SEQ ID NOS: 15

<210> SEQ ID NO 1
<211> LENGTH: 407
<212> TYPE: DNA
<213> ORGANISM: Christensenellaceae

<400> SEQUENCE: 1

```
tggggaatat tgggcaatgg gcgaaagcct tacccagcaa cgccgcgtga gggaagaagg      60
ttttcggatt gtaaacctct gtcctggggg acgaaggaag tgacggtacc ccggaggaa      120
gccccggcta actacgtgcc agcagccgcg gtaatacgta gggggcgagc gttgtccgga     180
attattgggc gtaaagggcg cgtagacggc tgtgtaagtt ataggtgaaa gcccaacttt     240
caaggttgga actgcctgta atactgcatg gcttgagtgc aggagaggga agcggaattc     300
ctagtgtagc ggtgaaatgc gtagatatta ggaggaacac cagtggcgaa ggcggctttc     360
tggactgtaa ctgacgttga ggcgcgaaag cgtggggagc aaacagg                   407
```

<210> SEQ ID NO 2
<211> LENGTH: 407
<212> TYPE: DNA
<213> ORGANISM: Christensenellaceae

<400> SEQUENCE: 2

```
ggggaatat tgggcaatgg gggaaaccct gacccagcaa cgccgcgtga aggaagaagg       60
ccttcgggtt gtaaacttct gtgacagggg acgaaggaag tgacggtacc ctgagaggaa     120
gctccggcaa actacgtgcc agcagccgcg gtaatacgta gggagcgagc gttgtccgga    180
attactgggc gtaaagggcg cgtaggcggt agatcaagtc gcatgtgaaa tacccgggct    240
caacctgggg ggtgcatgcg aaactggaat acttgagtgc ggtagaggaa agtggaattc    300
ctagtgtagc ggtgaaatgc gtagatatta ggaggaacac cagtggcgaa ggcgactttc    360
tgggccgtaa ctgacgctga ggcgcgaaag cgtggggagc aaacagg                  407
```

<210> SEQ ID NO 3
<211> LENGTH: 407
<212> TYPE: DNA
<213> ORGANISM: Christensenellaceae

<400> SEQUENCE: 3

```
tggggaatat tgggcaatgg gcgcaagcct gacccagcaa cgccgcgtga gggaagaagg      60
ttttcggatt gtaaacctct gtcgcagaag acgaaggaag tgacggtatt ctgtgaggaa    120
gccccggcta actacgtgcc agcagccgcg gtaatacgta gggggcgagc gttgtccgga    180
attactgggc gtaaagggag cgtaggcggt ctgataagtt ggatgtgaaa tacccgggct    240
taacttgggg ggtgcatcca atactgttgg actagagtac aggagaggaa agcggaattc    300
ctagtgtagc ggtgaaatgc atagatatta ggaggaacat cggtggcgaa ggcggctttc    360
tggactgcaa ctgacgctga ggctcgaaag cgtggggagc aaacagg                  407
```

<210> SEQ ID NO 4
<211> LENGTH: 407
<212> TYPE: DNA
<213> ORGANISM: Christensenellaceae

<400> SEQUENCE: 4

```
tagggaatat tggacaatgg ggggaaccct gatccagcaa cgccgcgtga aggaagaagg      60
tcttcggatt gtaaacttat gttgtcgggg acgaagaaag acgtacccg acgaggaagc     120
```

```
cccggctaac tacgtgccag cagccgcggt aatacgtagg gggcgagcgt tgtccggaat    180
tactgggcgt aaagggcgcg taggcggcat attaagttag atgtgaaatc cccgggctta    240
acctgggtgt tgcatttaaa actgataagc ttgagtgcag gagagggaag cggaattcct    300
agtgtagcgg tggaatgcgt agatattagg aggaacacca gtggcgaagg cggctttctg    360
gactgtaact gacgctgagg cgcgagagcg tggggagcaa acaggcc                  407
```

```
<210> SEQ ID NO 5
<211> LENGTH: 407
<212> TYPE: DNA
<213> ORGANISM: Christensenellaceae

<400> SEQUENCE: 5
tagggaatat tgggcaatgg gcgcaagcct gacccagcaa cgccgcgtga gggaagaagg     60
ttttcggatt gtaaacctct gtcctatgtg acgaaggaag tgacggtagc ataggaggaa    120
gccccggcta actacgtgcc agcagccgcg gtaatacgta gggggcgagc gttgtccgga    180
attactgggc gtaaagggtg cgtaggcggt ttggtaagtt ggatgtgaaa tacccgggct    240
taacttgggg gctgcatcca atactgtcgg acttgagtgc aggagaggaa agcggaattc    300
ctagtgtagc ggtgaaatgc gtagatatta ggaggaacac cagtggcgaa ggcggcttgc    360
tggacagtaa ctgacgctga ggcgcgaaag cgtggggagc aaacagg                  407
```

```
<210> SEQ ID NO 6
<211> LENGTH: 407
<212> TYPE: DNA
<213> ORGANISM: Christensenellaceae

<400> SEQUENCE: 6
tagggaatat tgggcaatgg gcgcaaccct gacccagcaa cgccgcgtga gggaagaagg     60
ttctctggat tgtaaacctc tgtcctatgg gacgaagaag tgacggtacc ataggaggaa    120
gctccggcta actacgtgcc agcagccgcg gtaatacgta gggagcgagc gttgtccgga    180
attactgggc gtaaagggtg cgtaggcggc ctggtaagtc agatgtgaaa tacccgtgct    240
caacatgggg ggtgcatctg atactgttag gcttgagtgc aggagaggaa agcggaattc    300
ctagtgtagc ggtgaaatgc gtagatatta ggaggaacac cagtggcgaa ggcggctttc    360
tggactgtaa ctgacgctga ggcacgaaag cgtggggagc aaacagg                  407
```

```
<210> SEQ ID NO 7
<211> LENGTH: 407
<212> TYPE: DNA
<213> ORGANISM: Christensenellaceae

<400> SEQUENCE: 7
tggggaatat tgggcaatgg gggcaaccct gacccagcaa cgccgcgtga gggaagaagg     60
ttttcggatt gtaaacctct gtccttgggg acgaagaagt gacggtaccc aaggaggaag    120
ctccggctaa ctacgtgcca gcagccgcgg taatacgtag ggagcgagcg ttgtccggaa    180
ttactgggcg taaagggtgc gtaggcggtt tggtaagtca gatgtgaaat acccgggctt    240
aacccggggg ctgcatctga tactgtcaga cttgagtgca ggagaggaaa gcggaattcc    300
tagtgtagcg gtgaaatgcg tagatattag gaggaacacc agtggcgaag gcggctttct    360
ggactgtaac tgacgctgag gcacgaaagc gtggggagca aacaggg                  407
```

```
<210> SEQ ID NO 8
```

```
<211> LENGTH: 407
<212> TYPE: DNA
<213> ORGANISM: Christensenellaceae

<400> SEQUENCE: 8
tcgggaatat tggacaatgg gggaaaccct gatccagcaa cgccgcgtga aggaagaagg      60
tcttcggatt gtaaacttat gttgtcgggg acgaagaaag acggtacccg acgaggaagc     120
cccggctaac tacgtgccag cagccgcggt aatacgtagg gggcgagcgt tgtccggaat     180
tactgggcgt aaagggcgcg taggcggcca attaagttag atgtgaaatc cccgggctta     240
acctgggtgt tgcatttaaa actgataggc ttgagtgcag gagagggaag cggaattcct     300
agtgtagcgg tggaatgcgt agatattagg aggaacacca gtggcgaagg cggctttctg     360
gactgtaact gacgctgagg cgcgagagcg tggggagcaa acaggcc                   407

<210> SEQ ID NO 9
<211> LENGTH: 407
<212> TYPE: DNA
<213> ORGANISM: Christensenellaceae

<400> SEQUENCE: 9
tggggaatat tggcaatgg gcggaagcct gacccagcaa cgccgcgtga gggaagaagg       60
ttttcggatt gtaaacctct gtcgcagaag acgaaggaag tgacggtatt ctgtgaggaa     120
gccccggcta actacgtgcc agcagccgcg gtaatacgta gggggcgagc gttgtccgga     180
attactgggc gtaaagggtg cgtaggcggt tgcttaagtt ggatgtgaaa tacccgggct     240
taacttgggg ggtgcattca agactgggga actagagtac aggagaggga agcggaattc     300
ctagtgtagc ggtgaaatgc gtagatatta ggaggaacac cggtggcgaa ggcggctttc     360
tggactgaca ctgacgctga ggcacgaaag cgtgggagc aaacagg                    407

<210> SEQ ID NO 10
<211> LENGTH: 407
<212> TYPE: DNA
<213> ORGANISM: Christensenellaceae

<400> SEQUENCE: 10
tggggaatat tgggcaatgg gcgcaagcct gacccagcaa cgccgcgtga gggaagaagg      60
ttttcggatc gtaaacctct gttgcagggg acgaggagta gacggtaccc tacgaggaag    120
ctccggctaa ctacgtgcca gcagccgcgg taatacgtag ggagcaagcg ttgtccggaa    180
tgactgggcg taaagggcgc gtaggtggtt ttgtaagtct ggagtgaaac cccgttttc     240 aaggcgggc ctgctttgga gactgcagga cttgagtgat ggagaggata gcggaattcc     300
cggtgtagcg gtgaaatgcg tagagatcgg gaggaacacc agtggcgaag gcggctatct    360
ggacatagac tgacactgag gcgcgaaagc gtggggagca acaggc                    407

<210> SEQ ID NO 11
<211> LENGTH: 407
<212> TYPE: DNA
<213> ORGANISM: Christensenellaceae

<400> SEQUENCE: 11
tggggaatat tgggcaatgg gcgcaagcct gacccagcaa cgccgcgtga gggaagaagg      60
tcttcggatt gtaaacctct gtcgcaaggg acgaaggcgt gacggtacct tgtgaggaag    120
ccccggctaa ctacgtgcca gcagccgcgg taatacgtag gggcgagcg ttgtccggaa     180 ttactgggcg taaagggtgc gtaggcggtt gcttaagttg gatgtgaaat acccggctt     240
```

```
aacttggggg gtgcattcaa aactgggcga ctagagttca ggagagggaa gcggaattcc      300
tagtgtagcg gtgaaatgcg tagatattag gaggaacacc agtggcgaag gcggctttct      360
ggactataac tgacgctgag gcacgaaagc gtggggagca aacaggc                    407
```

<210> SEQ ID NO 12
<211> LENGTH: 407
<212> TYPE: DNA
<213> ORGANISM: Christensenellaceae

<400> SEQUENCE: 12

```
tggggaatat tgggcaatgg gcgcaaccct gacccagcaa cgccgcgtga gggaagaagg      60
ttttcggatt gtaaacctct gtcgcagaag acgaaggaag tgacggtatt ctgtgaggaa     120
gccccggcta actacgtgcc agcagccgcg gtaatacgta gggggcgagc gttgtccgga     180
attactgggc gtaaagggtg cgtaggcggt taattaagtt ggatgtgaaa ttcccgggct     240
taacttggga gctgcattca aaactggtta actagagttc aggagaggga agcggaattc     300
ctagtgtagc ggtgaaatgc gtagatatta ggaggaacac cagtggcgaa ggcgacttac     360
tggacgaaca ctgacgctga ggcacgaaag cgtggggagc aaacagg                   407
```

<210> SEQ ID NO 13
<211> LENGTH: 407
<212> TYPE: DNA
<213> ORGANISM: Christensenellaceae

<400> SEQUENCE: 13

```
tggggaatat tgggcaatgg gcgcaagcct gacccagcaa cgccgcgtga aggaagaagg      60
tcttcggatt gtaaacttttt gtcgccggga acgataatga cggtacccgg taagaaagcc    120
ccggctaact acgtgccagc agccgcgtaa atacgtaggg ggcgagcgtt gtccggaatt    180
actgggcgta aagggcgcgt aggcggccgg ataagttaga tgtgaaatcc ccgggctcaa     240
cctgggtgtt gcatttaaaa ctgtctggct tgagtgcagg agaggaaagc ggaattccta     300
gtgtagcggt gaaatgcgta gatattagga ggaacatcag tggcgaaggc ggctttctgg     360
actgtaactg acgctgaggc gcgaaagcgt ggggagcaaa caggccc                   407
```

<210> SEQ ID NO 14
<211> LENGTH: 407
<212> TYPE: DNA
<213> ORGANISM: Christensenellaceae

<400> SEQUENCE: 14

```
tggggaatat tgggcaatgg gcgaaagcct gacccagcaa cgccgcgtga gggaagaagg      60
ccttcgggtt gtaaacctct gtccttagtg acgaaggaag tgacggtagc taaggaggaa     120
gccccggcta actacgtgcc agcagccgcg gtaatacgta gggggcgagc gttgtccgga     180
attactgggc gtaaagggtg cgtaggcggt actttaagtt ggatgtgaaa tcccgggct     240 taacctgggg cctgcatcca atactggaga actagagtgc aggagaggga agcggaattc     300
ctagtgtagc ggtgaaatgc gtagatatta ggaagaacac cagtggcgaa ggcggctttc     360
tggactgtaa ctgacgctga ggcacgaaag cgtggggagc aaacagg                   407
```

<210> SEQ ID NO 15
<211> LENGTH: 407
<212> TYPE: DNA
<213> ORGANISM: Christensenellaceae

```
<400> SEQUENCE: 15
tggggaatat tgcgcaatgg gcgcaagcct gacgcagcaa cgccgcgtga gggaagaagg      60
ctttcgggtt gtaaacctct gtccttggtg acgaaggaag tgacggtagc caaggaggaa     120
gccccggcta actacgtgcc agcagccgcg gtaatacgta gggggcgagc gttgtccgga     180
attactgggc gtaaagggtg cgtaggcggt ctattaagtt ggatgtgaaa tccccgggct     240
taacttgggg tctgcatcca atactgggag actagagtgc aggagaggga agcggaattc     300
ctagtgtagc ggtgaaatgc gtagatatta ggaggaacac cagtggcgaa ggcggctttc     360
tggactgtaa ctgacgctga ggcacgaaag cgtggggagc aaacagg                  407
```